United States Patent
Wang et al.

(10) Patent No.: US 11,059,772 B2
(45) Date of Patent: Jul. 13, 2021

(54) IMINE-TYPE QUATERNARY AMMONIUM SALT CATALYST, PREPARATION METHOD THEREOF AND USE THEREOF FOR PREPARATION OF POLYISOCYANATE COMPOSITION

(71) Applicant: Wanhua Chemical Group Co., Ltd., Shandong (CN)

(72) Inventors: Nuancheng Wang, Shandong (CN); Yonghua Shang, Shandong (CN); Yuqi Wang, Shandong (CN); Bin Shi, Shandong (CN); Zhicheng Zhu, Shandong (CN); Hefu Li, Shandong (CN); Yuan Li, Shandong (CN); Weiqi Hua, Shandong (CN)

(73) Assignee: Wanhua Chemical Group Co., Ltd.

( * ) Notice: Subject to any disclaimer, the term of this patent is extended or adjusted under 35 U.S.C. 154(b) by 0 days.

(21) Appl. No.: 16/762,265

(22) PCT Filed: Feb. 13, 2018

(86) PCT No.: PCT/CN2018/076687
§ 371 (c)(1),
(2) Date: May 7, 2020

(87) PCT Pub. No.: WO2019/104888
PCT Pub. Date: Jun. 6, 2019

(65) Prior Publication Data
US 2020/0377445 A1 Dec. 3, 2020

(30) Foreign Application Priority Data
Nov. 30, 2017 (CN) .......................... 201711243688.6

(51) Int. Cl.
| | |
|---|---|
| *C08G 18/72* | (2006.01) |
| *C08G 18/78* | (2006.01) |
| *C07C 211/63* | (2006.01) |
| *B01J 31/04* | (2006.01) |

(52) U.S. Cl.
CPC ............ *C07C 211/63* (2013.01); *B01J 31/04* (2013.01); *C08G 18/72* (2013.01); *C08G 18/7818* (2013.01); *C08G 18/7837* (2013.01); *C08G 18/7843* (2013.01); *C08G 18/7887* (2013.01); *C08G 18/7893* (2013.01); *B01J 2231/14* (2013.01); *B01J 2531/002* (2013.01)

(58) Field of Classification Search
CPC ............ C08G 18/7843; C08G 18/7837; C08G 18/7893; C08G 18/7887; C08G 18/7818; C08G 18/72
See application file for complete search history.

(56) References Cited

U.S. PATENT DOCUMENTS

| | | | |
|---|---|---|---|
| 5,124,427 A | 6/1992 | Potter et al. | |
| 5,489,663 A | 2/1996 | Brandt et al. | |
| 5,914,383 A * | 6/1999 | Richter | C07D 251/32 528/59 |
| 6,800,714 B2 | 10/2004 | Kohlstruk et al. | |
| 7,001,973 B2 | 2/2006 | Kohlstruk et al. | |
| 7,834,103 B2 * | 11/2010 | Asahina | C08G 18/792 525/453 |
| 9,926,402 B2 * | 3/2018 | Laas | C08G 18/222 |
| 9,938,369 B2 * | 4/2018 | Richter | C07D 273/04 |
| 2003/0078450 A1 | 4/2003 | Kocher et al. | |
| 2003/0153714 A1 | 8/2003 | Kohlstruk et al. | |
| 2017/0253688 A1 * | 9/2017 | Yamauchi | C08G 18/02 |
| 2018/0244826 A1 | 8/2018 | Richter | |
| 2020/0040124 A1 * | 2/2020 | Azuma | C08G 18/807 |

FOREIGN PATENT DOCUMENTS

| | | |
|---|---|---|
| CN | 101165048 A | 4/2008 |
| CN | 101927184 A | 12/2010 |
| CN | 102718683 A | 10/2012 |
| CN | 105964301 A | 9/2016 |
| WO | 2017029266 A1 | 2/2017 |

OTHER PUBLICATIONS

International Search Report from Application No. PCT/CN2018/076687 dated Jul. 27, 2018, 2 pages.
National Standard of the People's Republic of China GB/T3143-82 "Color Determination method of liquid chemicals (Hazen unit—platinum-cobalt scale)" dated Jul. 20, 1982; Implemented on: Mar. 1, 1983; 3 pages English preview at https://www.google.com/books/edition/_/nLarCwAAQBAJ?hl=en&gbpv=1.
National Standard of the People's Republic of China GB/T12009. 4-89 "Polymethylene polyphenyl isocyanate—Determination of isocyanato content," Issued on Dec. 25, 1989; Implemented on Nov. 1, 1990; 3 pages.

* cited by examiner

*Primary Examiner* — Michael L Leonard
(74) *Attorney, Agent, or Firm* — Lerner, David, Littenberg, Krumholz & Mentlik, LLP

(57) ABSTRACT

Disclosed is an imine-type quaternary ammonium salt catalyst, wherein the catalyst has a general structure formula shown by formula I below; in the formula, R1 and R2, respectively, are independently selected from a C1-C20 linear alkyl or a branched C3-C20 alkyl, and a C1-C20 hydroxylalkyl, a C3-C8 cycloalkyl, and arylated alkyl; R3 is a linear or branched alkyl, cycloalkyl or aryl; and R4 is hydrogen, aryl, a linear C1-C15 alkyl or branched C3-C15 alkyl. Also disclosed are a method for preparing the catalyst and a polyisocyanate composition prepared therefrom. The catalyst, by introducing an imine structure, on the basis of ensuring high catalytic activity thereof, is allowed to have properties of high temperature decomposition and inactivation, and when applied to the synthesis of polyisocyanate, can effectively prevent the risk of explosive polymerization caused by an uncontrolled reaction.

12 Claims, No Drawings

IMINE-TYPE QUATERNARY AMMONIUM SALT CATALYST, PREPARATION METHOD THEREOF AND USE THEREOF FOR PREPARATION OF POLYISOCYANATE COMPOSITION

CROSS REFERENCE TO RELATED APPLICATIONS

The present application is a national phase entry under 35 U.S.C. § 371 of International Application No. PCT/CN2018/076687, filed Feb. 13, 2018, which claims priority from Chinese Patent Application No. 201711243688.6 filed Nov. 30, 2017, all of which are hereby incorporated herein by reference.

TECHNICAL FIELD

The invention relates to the field of preparing polyisocyanate, specifically to an imine-type quaternary ammonium salt catalyst for preparing polyisocyanate compositions, preparation method of the catalyst, and polyisocyanate prepared by using the catalyst.

TECHNICAL BACKGROUND

Aliphatic diisocyanate compounds have irreplaceable advantages in the synthesis of anti-yellowing coatings and paint, and are widely used in coating industry. However, monomeric aliphatic isocyanates have a greater limitation on the application for their low vapor pressure, therefore, it is more common to modify them into a polyisocyanate to increase biological tolerance during processing and further obtain products with excellent performance.

Since isocyanurate has high thermal stability, strong radiation resistance, low viscosity and high crosslinking density, the self-polymerization of isocyanates has been widely studied in the past. These researches focus on how to find an efficient structural form for catalyst that can effectively reduce the amount of additives in the process of industrialization, thereby obtaining polyisocyanate products with high quality.

The catalysts used for isocyanate self-polymerization generally have the following structural characteristics:

Wherein the cation form can include alkali metal ions, alkaline earth metal ions, and an ion group structure with N and P as core and having the following characteristics:

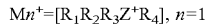

Wherein, $R_1$, $R_2$, $R_3$, and $R_4$ are the same or different, and optionally selected from alkyl or substituted alkyl having 1-20 carbon atoms, for example, U.S. Pat. Nos. 673,062, 6,800,714, and 7,001,973 all adopt quaternary ammonium salt cation in which $R_1$ contains a benzene derivative structure, $R_2$ and $R_3$ are alkyl or substituted alkyl or cycloalkyl, and $R_4$ is alkyl or cycloalkyl or alkoxy, and can efficiently synthesize products. However, it should be pointed out that the control of color number thereof still cannot meet the requirements of industrial production for low color number polyisocyanate compounds. U.S. Pat. No. 5,489,663 also uses a variety of designs for cation to obtain ideal color control effects, but its design for catalyst results in lower reaction activity and requires higher reaction temperature control, and when the temperature control is lower, the reaction time is doubled.

Commonly used anion in quaternary ammonium salt is $R_5COO^-$, $OH^-$, $F^-$, and can obtain trimer structures with the ideal structure, for example, U.S. Pat. No. 5,124,427 adopts the design of anion being $OH^-$, $F^-$, and the color number of the product is controlled between 40-80.

Patent CN101927184 discloses that when a quaternary ammonium/phosphine salt is used to compound with a six-membered heterocyclic compound of a weakly basic nitrogen-containing compound, a light-colored polyisocyanate compound with good quality can be efficiently prepared.

However, it should be pointed out that all the preparation processes reported in the above patents are terminated at the oligomerization stage and then the monomer is removed to obtain the qualified samples. From the perspective of process safety, this reaction has a potential and huge thermal cumulative effect, once the process control is out of control, it will cause huge economic losses and threaten personnel safety.

SUMMARY OF THE INVENTION

One of the objectives of the present invention is to provide an imine-type quaternary ammonium salt-type catalyst, starting from the design of the catalyst, by introducing an imine structure, the catalyst is allowed to have properties of high-temperature decomposition and deactivation on the basis of ensuring high catalytic activity; and when used in the synthesis of polyisocyanates, it can effectively prevent the risk of explosive polymerization caused by uncontrolled reactions.

Another objective of the present invention is to provide a method for preparing an imine-type quaternary ammonium salt-type catalyst, the prepared catalyst can effectively prevent the risk of explosive polymerization caused by uncontrolled reaction in the synthesis of polyisocyanates.

A further objective of the present invention is to provide a polyisocyanate composition prepared by using the above catalyst.

To achieve one aspect of the objectives mentioned above, the imine-type quaternary ammonium salt-type catalyst provided by the present invention adopts the following technical solution:

an imine-type quaternary ammonium salt catalyst, wherein, the catalyst has a general structural formula as shown in the following formula I:

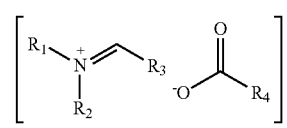

in the formula, $R_1$ and $R_2$ are independently selected from a linear C1-C20 (such as C3, C5, C8, C10, C12 or C15) alkyl or a branched C3-C20 (such as C5, C8, C10, C12 or C15) alkyl and a C1-C20 (such as C3, C5, C8, C10, C12, or C15) hydroxyl alkyl (also known as hydroxyalkyl), a C3-C8 (such as C4 or C6) cycloalkyl, and an arylated alkyl;

R3 is a linear or branched alkyl, cycloalkyl or aryl; for example a linear C1-C13 alkyl (such as a linear C1, C3, C7, C9, or C13 alkyl), or a branched C3-C15 alkyl (such as a branched C5, C8, C10, C12 or C15 alkyl), or a C3-C8 cycloalkyl (such as C4,C5, or C6), or an aryl such as phenyl, phenmethyl;

R4 is hydrogen, aryl, a linear C1-C15 (such as C3, C5, C8, C10 or C12) alkyl or a branched C3-C15 (such as C5, C8, C10 or C12) alkyl.

To achieve another aspect of the objectives mentioned above, the method for preparing an imine-type quaternary ammonium salt-type catalyst provided by the present invention adopts the following technical solution:

a method for preparing an imine-type quaternary ammonium salt catalyst, comprising the following steps:

(1) adding trimethylchlorosilane gradually into a di-substituted secondary amine under ice-water bath condition, after the addition, returning to room temperature and continuing the reaction, after the reaction, adding ice water into the reaction solution to quench the reaction, and separating to obtain an intermediate product a;

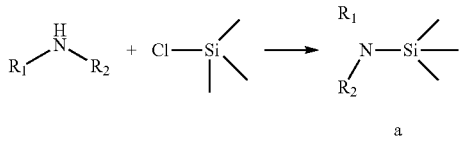

a (2) adding trimethylchlorosilane gradually into a carboxylic acid under ice-water bath condition, after the addition, returning to room temperature and continuing the reaction, after the reaction, adding ice water into the reaction solution to quench the reaction, and separating to obtain an intermediate product b;

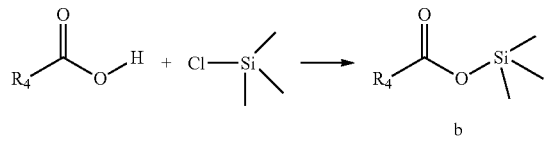

b (3) dissolving the separated intermediate product a, intermediate product b and a dimethyl acetal in an alcohol solvent, and reacting at 50-80° C., after the reaction is completed, optionally removing part of the alcohol solvent, and obtaining an alcohol solution containing the imine-type quaternary ammonium salt catalyst at a target concentration;

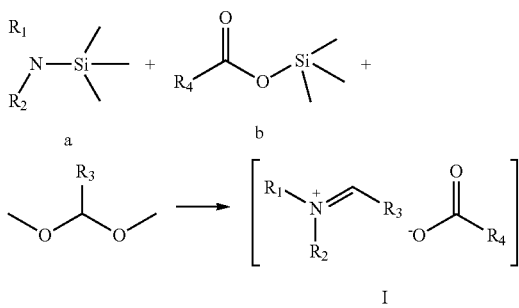

I preferably, the imine-type quaternary ammonium salt catalyst has a general structural formula as shown in Formula I described above.

Wherein, "optionally removing" means removing or not removing, and those skilled in the art will understand that it can be actually determined according to the target concentration of the catalyst.

According to the method for preparing the catalyst of the present invention, preferably, in step (1), the molar amount of trimethylchlorosilane is not less than the molar amount of the secondary amine, preferably 1-1.2 times of the molar amount of the secondary amine; in one embodiment, the intermediate product can be separated by extraction, for example, after the extraction with an extractant, drying and separating by distillation to obtain the intermediate product a; wherein the extractant is preferably selected from the group consisting of dichloromethane, ethyl acetate, chloroform and any combination thereof; the drying treatment is preferably performed by adding a drying agent such as anhydrous sodium sulfate and/or anhydrous magnesium sulfate.

According to the method for preparing the catalyst of the present invention, preferably, the reaction in step (1) is controlled to be continued for 0.5-2 h, such as 1 or 1.5 h, after returning to room temperature and before quenching.

According to the method for preparing the catalyst of the present invention, preferably, in step (2), the molar amount of trimethylchlorosilane is not less than the molar amount of the carboxylic acid, and preferably 1-1.2 times of the molar amount of the carboxylic acid; in one embodiment, the intermediate product can be separated by extraction, for example, after the extraction with an extractant, drying and separating by distillation to obtain the intermediate product b; wherein the extractant is preferably selected from the group consisting of dichloromethane, ethyl acetate, chloroform and any combination thereof; the drying treatment is preferably performed by adding a drying agent such as anhydrous sodium sulfate and/or anhydrous magnesium sulfate.

According to the method for preparing the catalyst of the present invention, preferably, the reaction in step (2) is controlled to be continued for 0.5-1 h after returning to room temperature and before quenching.

According to the method for preparing the catalyst of the present invention, preferably, in step (3), the intermediate product a, intermediate product b, and dimethyl acetal are fed at substantially equimolar amounts; in the present invention, "substantially equimolar amounts" means that the difference between the feeding molar amounts of any two of the three materials does not exceed 10%, preferably 5%, and further preferably 2% of the smaller one of them.

According to the method for preparing the catalyst of the present invention, the reaction in step (3) is preferably performed at 50-80° C., such as 60 or 70° C. for 3-8 h, such as for 4, 5 or 6 h.

Preferably, the alcohol solvent is a monohydric alcohol and/or a dihydric alcohol; wherein the monohydric alcohol is preferably selected from the group consisting of a C1-C10-aliphatic, cycloaliphatic, araliphatic and aromatic alcohol or phenol, and the monohydric alcohol is preferably in the form of a linear, branched, or cyclic alcohol or phenol; the dihydric alcohol is, not limited to the follows, for example, ethylene glycol, 1,3-propanediol, 1,2-propanediol, 1,3-butanediol, 1,4-butanediol, 2,3-butanediol, 1,5-pentanediol, 1,2-pentanediol, 1,3-pentanediol, 1,4-pentanediol, neopentyl glycol, 1,6-hexanediol, 1,7-heptanediol, 1,8-octanediol, 1,9-nonanediol, 1,10-decanediol, diethylene glycol, polyethylene glycol, polypropylene glycol, polytetramethylene glycol, 2-methyl-1,3-propanediol, 3-methyl-1,5-pentanediol, 2-methyl-1,8-octanediol and 2,2-diethyl-1,3-propanediol.

To achieve still another aspect of the objectives mentioned above, the present invention also provides a polyisocyanate composition prepared by using the catalyst described above; preferably adopting the following technical solution:

A polyisocyanate composition, wherein, the polyisocyanate composition has isocyanurate, urethane, allophanate, and iminooxadiazinedione groups, wherein the molar ratio of allophanate group/(isocyanurate group+allophanate group) is 0.1-0.8, preferably 0.2-0.6, such as 0.3, 0.4 or 0.5; the molar ratio of allophanate group/(allophanate group+urethane group) is 0.1-0.7, preferably 0.2-0.5, such as 0.3 or 0.4; the molar ratio of iminooxadiazinedione group/isocyanurate group is 0.005- 0.15, preferably 0.01-0.1, such as 0.02, 0.05 or 0.08.

The composition according to the present invention, wherein, is prepared by the oligomerization of at least one kind of isocyanate monomer having a NCO functionality >1 in the presence of the above-mentioned imine-type quaternary ammonium salt catalyst. The oligomerization reaction is well known in the art, for example, the polymerization reaction not exceeding tetramerization.

According to the composition of the present invention, preferably, the isocyanate monomer is selected from aliphatic diisocyanate, preferably is one or more of hexamethylene diisocyanate (HDI), 2-methylpentane-1,5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), and 1,3- and 1,4-bis(isocyanatomethyl)cyclohexane (H6XDI).

To better promote the target reaction, according to the composition of the present invention, preferably, the catalyst is added in the form of an alcohol solution during the preparation process, preferably, the mass concentration of the catalyst in the alcohol is 0.25%-50%, such as 1%, 5%, 10%, 15%, 20%, 30% or 40%; the amount of the catalyst used is from 0.001 to 5%, preferably 0.002-2%, such as 0.1%, 0.5%, 1%, or 1.5% of the mass of the organic isocyanate.

According to the composition of the present invention, preferably, the oligomerization is performed in a temperature ranging from 0° C. to 100° C., preferably 20-90° C., such as 30, 50 or 70° C.

According to the composition of the present invention, preferably, the oligomerization is terminated after converting 5-80 wt %, preferably 10 - 70 wt %, such as 40 wt % or 50 wt % of the isocyanate monomer; further preferably, the oligomerization is terminated by deactivating the catalyst, it is further preferred that the catalyst is deactivated by thermal decomposition or by adding an acid or an acid derivative; wherein, the added acid or acid derivative is such as benzoyl chloride, acid ester of an acid containing phosphorus or sulfur, and the acids themselves; and it is particularly preferred that the catalyst is deactivated by thermal decomposition. In the present invention, after the reaction is terminated, the unreacted monomer of organic isocyanate can be separated from the reaction mixture for recycling.

The positive effects of the present invention are that, starting from the design of the catalyst, by introducing an imine structure, the catalyst is allowed to have properties of high-temperature decomposition and deactivation on the basis of ensuring high catalytic activity; and when applied to the synthesis of polyisocyanates, the catalyst can effectively prevent the risk of explosive polymerization caused by uncontrolled reactions.

At the same time, the polyisocyanate composition of the present invention prepared by using the catalyst described above has isocyanurate, urethane, allophanate, iminooxadiazine dione group in a certain proportion range, and exhibits the properties of excellent moisture resistance and thinning stability.

EMBODIMENTS

A further explanation for the invention is given below in combination with examples. It should be noted that these examples do not constitute a limitation on the protection scope claimed by the invention.

All percentages referred to in the invention are mass percentages unless otherwise specified.

The NCO content is measured according to the method of GB/T 12009.4-1989 in the present invention.

The color number of products is measured according to the method of GB/T 3143-1982 in the present invention.

For each molar ratio of the isocyanurate group, urethane group, allophanate group, and iminooxadiazine dione group in the polyisocyanate composition (that is, isocyanate curing agent) of the present invention, AVANCE400 manufactured by Bruker Biospin was used, and deuterated chloroform $CDCl_3$ was used as a solvent, and a $^{13}C$ nuclear magnetic resonance spectrum was measured overnight with a sample (polyisocyanate composition) at a concentration of 60% by mass, under the condition of 100 MHz.

It should be noted that, in the above measurement, the integrated value of the following signals was divided by the number of carbons measured, from which each molar ratio was calculated.

Isocyanurate group: near 148.6 ppm
Allophanate group: near 154 ppm
Urethane group: near 156.5 ppm
Iminooxadiazine dione group: near 137.3 ppm Molar ratio 1: allophanate group/(allophanate group+isocyanurate group)=(signal area near 154 ppm)/(signal area near 154 ppm+signal area near 148.6/3)

Molar ratio 2: allophanate group/(allophanate group+urethane group)=(signal area near 154 ppm)/(signal area near 154 ppm+signal area near 156.5 ppm)

Molar ratio 3: iminooxadiazine dione group/isocyanurate group=signal area near 137.3 ppm/(signal area near 148.6/3)

The dynamic viscosity in the present invention is obtained by employing a Brookfield DV-I Prime viscomete with a S21 rotor at 25° C. According to a literature report (CN200710180169.X), different shear rates can ensure that the rheological data of the polyisocyanate of the present invention conforms to ideal fluid behavior, so the shear rates are not specifically provided here.

All the reagents used in the synthesis process of the present invention were purchased from Sigma-Aldrich, unless otherwise specified, were all analytically pure.

EXAMPLE 1

Preparation of Catalyst I
(1) 12 parts (parts by weight, similarly hereinafter) of trimethylchlorosilane were added dropwise to 5 parts of dimethylamine under ice-water bath condition, after the dropwise addition, the temperature was returned to room temperature and the reaction was continued for 0.5 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product I-a;

(2) 12 parts of trimethylchlorosilane were added dropwise to 16 parts of 2-ethylhexanoic acid under ice-water bath condition, after the dropwise addition, the temperature was returned to room temperature and the reaction was continued for 1 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product I-b;

(3) the separated intermediate product I-a, intermediate product I-b and 13 parts of dimethyl-n-butyral were dissolved in 243 parts of n-hexanol solution, and reacted at 50° C. for 5 hours, after the reaction, a solution of 10% catalyst I in n-hexanol was obtained.

The structure of catalyst I was as follows:

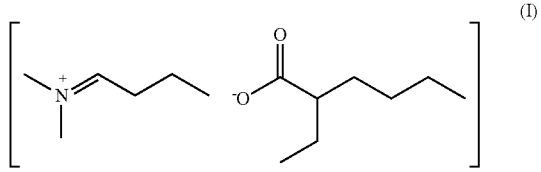

(I)

EXAMPLE 2

Preparation of Catalyst II (1) 12 parts of trimethylchlorosilane were added dropwise to 6.5 parts of methyl ethylamine under ice-water bath condition, after the dropwise addition, the temperature was returned to room temperature and the reaction was continued for 0.5 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product II-a;

(2) 12 parts of trimethylchlorosilane were added dropwise to 16 parts of 2-ethylhexanoic acid under ice-water bath condition, after the dropwise addition, the temperature was returned to room temperature and the reaction was continued for 1 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product II-b;

(3) the separated intermediate product a, intermediate product b and 16.8 parts of dimethyl benzalation were dissolved in 32 parts of methanol solution and reacted at 50° C. for 8 hours, after the reaction, a solution of 50% catalyst II in methanol was obtained.

The structure of catalyst II was as follows:

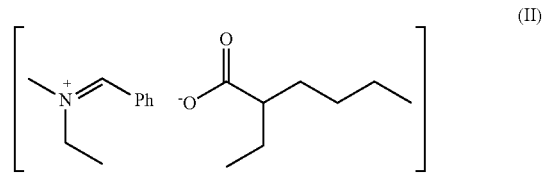

(II)

EXAMPLE 3

Preparation of Catalyst III (1) 12 parts of trimethylchlorosilane were added dropwise to 15 parts of N-(4-ethylbenzyl)ethylamine under ice-water bath condition, after the dropwise addition, the temperature was returned to room temperature and the reaction was continued for 3 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product III-a;

(2) 12 parts of trimethylchlorosilane were added dropwise to 4.24 parts of formic acid under ice-water bath condition, after the dropwise addition, the temperature was returned to room temperature and the reaction was continued for 1 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product III-b;

(3) the separated intermediate product a, intermediate product b and 8.3 parts of dimethylacetal were dissolved in 2144 parts of 1,3-butanediol solution and reacted at 70° C. for 8 hours, after the reaction, a solution of 1% catalyst III in 1,3-butanediol was obtained.

The structure of catalyst III was as follows:

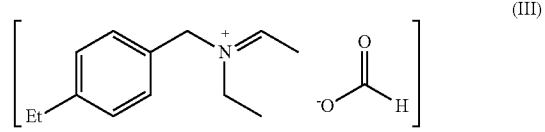

(III)

EXAMPLE 4

Preparation of Catalyst IV (1) 12 parts of trimethylchlorosilane were added dropwise to 16 parts of N-methyl-2-indane under ice-water bath condition, after the dropwise addition, the temperature was returned to room temperature and the reaction was continued for 1.5 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product IV-a;

(2) 12 parts of trimethylchlorosilane were added dropwise to 8.1 parts of butyric acid under ice-water bath condition, after the dropwise addition, the temperature was returned to room temperature and the reaction was continued for 1 h, after the reaction, 50 parts of ice water were added into the reaction solution to quench the reaction, and an organic phase was obtained after extraction with dichloromethane. The organic phase was dried by adding 10 parts of anhydrous sodium sulfate, and then the organic phase was distilled to remove solvent under reduced pressure to obtain an intermediate product IV-b;

(3) the separated intermediate product a, intermediate product b and 15.9 parts of dimethylcyclopentylaldehyde were dissolved in 133.2 parts of 2-ethyl hexanol solution and reacted at 80° C. for 8 hours, after the reaction, a solution of 20% catalyst IV in 2-ethyl hexanol was obtained.

The structure of catalyst IV was as follows:

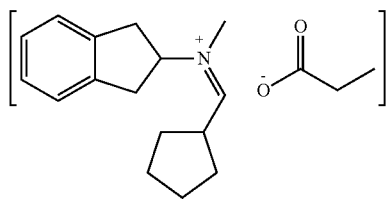

(IV)

EXAMPLE 5

Preparation of Catalyst V (1) 12 parts of trimethylchlorosilane were added dropwise to 5 parts of dimethylamine under ice-water bath condition, after the dropwise addition, the temperature was returned to room temperature and the reaction was continued for 0.5 h, after the reaction, 50 parts of ice water were added into the reaction solution to quench the reaction, and an organic phase was obtained after extraction with ethyl acetate. The organic phase was dried by adding 10 parts of anhydrous sodium sulfate, and then the organic phase was distilled to remove solvent under reduced pressure to obtain an intermediate product V-a;

(2) 12 parts of trimethylchlorosilane were added dropwise to 13.5 parts of benzoic acid under ice-water bath condition, after the dropwise addition, the temperature was returned to room temperature and the reaction was continued for 1 h, after the reaction, 50 parts of ice water were added into the reaction solution to quench the reaction, and an organic phase was obtained after extraction with ethyl acetate. The organic phase was dried by adding 10 parts of anhydrous magnesium sulfate, and then the organic phase was distilled to remove solvent under reduced pressure to obtain an intermediate product V-b;

(3) the separated intermediate product a, intermediate product b and 8.3 parts of dimethylacetal were dissolved in a solution of 4269 parts of ethylene glycol and 4269 parts of n-butanol, and reacted at 60° C. for 8 hours, after the reaction, a mixed alcohol solution of 0.25% catalyst V was obtained.

The structure of catalyst V was as follows:

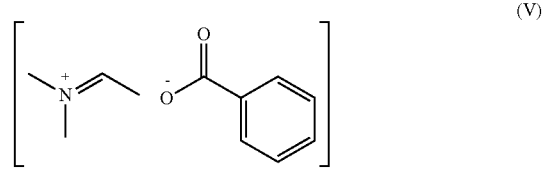

(V)

EXAMPLE 6

600 g of HDI was degassed for 10 min under the condition of 20° C./50 mbar. Under nitrogen protection, the treated HDI was preheated to 60° C., and 1.2 g of the solution of 10% catalyst I in hexanol was added dropwise to the HDI, the temperature of the system was controlled to 60-65° C., and the NCO % change was monitored during the reaction. The reaction was terminated by adding 0.12 g of phosphoric acid when the value of NCO % dropped to 38. The reaction solution was subjected to thin film evaporation to remove residual monomers to obtain about 260 g of an isocyanate curing agent.

Product index:
Viscosity: 1650 cp/25° C.
NCO %: 22.2%
Color number: 20 Hazen
Free monomer: 0.03%

In the prepared curing agent, the molar ratio of allophanate group/(isocyanurate group+allophanate group) is 0.1; the molar ratio of allophanate group/(allophanate group+urethane group) is 0.7; the molar ratio of iminooxadiazinedione group/isocyanurate group is 0.1.

EXAMPLE 7

600 g of HDI was degassed for 10 min under the condition of 20° C./50 mbar. Under nitrogen protection, the treated HDI was preheated to 60° C., and 4.0 g of the solution of 3% catalyst II in hexanol was added dropwise to the HDI, the temperature of the system was controlled to 60-65° C., and the NCO % change was monitored during the reaction. When the value of NCO % dropped to 38, the temperature of the reaction was raised to 100° C. within 20 minutes, and within 1 hour thereafter, the NCO % no longer changed, the catalyst was deactivated by heat, and the reaction was terminated. The reaction solution was subjected to thin film evaporation to remove residual monomers to obtain about 260 g of an isocyanate curing agent.

Product index:
Viscosity: 1700 cp/25° C.
NCO %: 22.1%
Color number: 20 Hazen
Free monomer: 0.04%

In the prepared curing agent, the molar ratio of allophanate group/(isocyanurate group+allophanate group) is 0.1; the molar ratio of allophanate group/(allophanate group+urethane group) is 0.7; the molar ratio of iminooxadiazinedione group/isocyanurate group is 0.1.

EXAMPLE 8

600 g of HDI was degassed for 10 min under the condition of 20° C./50 mbar. Under nitrogen protection, the treated HDI was preheated to 60° C., and 6 g of the solution of 1% catalyst III in 1,3-butanediol was added dropwise to the HDI, the temperature of the system was controlled to 60-65°

C., and the NCO % change was monitored during the reaction. When the value of NCO % dropped to 38, the temperature of the reaction was raised to 100° C. within 20 minutes, and within 1 hour thereafter, the NCO % no longer changed, the catalyst was deactivated by heat, and the reaction was terminated. The reaction solution was subjected to thin film evaporation to remove residual monomers to obtain about 240 g of an isocyanate curing agent.
Product index:
Viscosity: 2800 cp/25° C.
NCO %: 21.0%
Color number: 18 Hazen
Free monomer: 0.03%
In the prepared curing agent, the molar ratio of allophanate group/(isocyanurate group+allophanate group) is 0.3; the molar ratio of allophanate group/(allophanate group+urethane group) is 0.6; the molar ratio of iminooxadiazinedione group/isocyanurate group is 0.08.

EXAMPLE 9

600 g of HDI was degassed for 10 min under the condition of 20° C./50 mbar. Under nitrogen protection, the treated HDI was preheated to 60° C., and 30 g of the solution of 20% catalyst IV in 2-ethylhexanol was added dropwise to the HDI, the temperature of the system was controlled to 70-75° C., and the NCO % change was monitored during the reaction. When the value of NCO % dropped to 36, the temperature of the reaction was raised to 100° C. within 20 minutes, and within 1 hour thereafter, the NCO % no longer changed, the catalyst was deactivated by heat, and the reaction was terminated. The reaction solution was subjected to thin film evaporation to remove residual monomers to obtain about 260 g of an isocyanate curing agent.
Product index:
Viscosity: 600 cp/25° C.
NCO %: 19.8%
Color number: 16 Hazen
Free monomer: 0.03%
In the prepared curing agent, the molar ratio of allophanate group/(isocyanurate group+allophanate group) is 0.65; the molar ratio of allophanate group/(allophanate group+urethane group) is 0.65; the molar ratio of iminooxadiazinedione group/isocyanurate group is 0.12.

EXAMPLE 10

600 g of HDI was degassed for 10 min under the condition of 20° C./50 mbar. Under nitrogen protection, the treated HDI was preheated to 60° C., and 20 g of the solution of 0.5% catalyst IV in 2-ethyl-1,3-hexanediol was added dropwise to the HDI, the temperature of the system was controlled to 60-65° C., and the NCO % change was monitored during the reaction. When the value of NCO % dropped to 30, the temperature of the reaction was raised to 100° C. within 20 minutes, and within 1 hour thereafter, the NCO % no longer changed, the catalyst was deactivated by heat, and the reaction was terminated. The reaction solution was subjected to thin film evaporation to remove residual monomers to obtain about 360 g of an isocyanate curing agent.
Product index:
Viscosity: 8000 cp/25° C.
NCO %: 18.5%
Color number: 21 Hazen
Free monomer: 0.03%
In the prepared curing agent, the molar ratio of allophanate group/(isocyanurate group+allophanate group) is 0.52; the molar ratio of allophanate group/(allophanate group+urethane group) is 0.5; the molar ratio of iminooxadiazinedione group/isocyanurate group is 0.1.

Comparative Example 1

600 g of HDI was degassed for 10 min under the condition of 20° C./50 mbar. Under nitrogen protection, the treated HDI was preheated to 60° C., and 0.3 g of a solution of 40% commercial N, N, N-trimethyl-N-benzyl ammonium hydroxide in methanol was added dropwise to the HDI, the temperature of the system was controlled to 60-65° C., and the NCO % change was monitored during the reaction. The reaction was terminated by adding 0.06 g of phosphoric acid when the value of NCO % dropped to 42. The reaction solution was subjected to thin film evaporation to remove residual monomers to obtain about 230 g of an isocyanate curing agent.
Product index:
Viscosity: 2000 cp/25° C.
NCO %: 22.0%
Color number: 22 Hazen
Free monomer: 0.05%

EXAMPLE 11

30 g of the products prepared in Examples 6, 7, 8, 9, and 10 were weighed into different glass bottles (the capacity of the glass bottle is 150 mL) respectively, then 70 g of butyl acetate with a water content of 1000 ppm and 0.05 g of DBTL were added thereto respectively, and after stirring evenly, the container was sealed and placed in a incubator at 35° C. to observe the gelation time of the product.

| Name of Sample | Gelation time |
| --- | --- |
| Product of Example 6 | 3.5 h |
| Product of Example 7 | 3.0 h |
| Product of Example 8 | 5 h |
| Product of Example 9 | 4.5 h |
| Product of Example 10 | 4 h |
| Product of Comparative Example 1 | 2 h |

It can be seen from the above Examples:

The polyisocyanate composition of the present invention exhibits characteristics of excellent moisture resistance and thinning stability, at the same time, the preparation process thereof starts from the design of the catalyst, the catalyst is allowed to have properties of high-temperature (100° C.) decomposition and deactivation by introducing an imine structure, therefore, when applied to the synthesis of polyisocyanates, the catalyst can effectively prevent the risk of explosive polymerization caused by uncontrolled reactions, and at the same time, the catalyst still maintains high catalytic activity at normal reaction temperature range.

The invention claimed is:
1. A polyisocyanate composition, characterized in that, the polyisocyanate composition has isocyanurate, urethane, allophanate, and iminooxadiazinedione groups, wherein the molar ratio of allophanate group/(isocyanurate group+allophanate group) is 0.1-0.8; the molar ratio of allophanate group/(allophanate group+urethane group) is 0.1-0.7; the molar ratio of iminooxadiazinedione group/isocyanurate group is 0.005-0.15.
2. A polyisocyanate composition according to claim 1, characterized in that, the polyisocyanate composition is prepared by the oligomerization of at least one kind of isocyanate monomer having a NCO functionality>1 in the presence of a quaternary ammonium salt catalyst which has a general structural formula as shown in the following formula I:

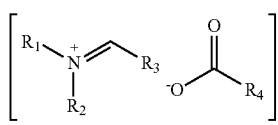

in the formula, $R_1$ and $R_2$ are independently selected from a linear C1-C20 alkyl or a branched C3-C20 alkyl and a C1-C20 hydroxyalkyl, a C3-C8 cycloalkyl, and an arylated alkyl;

R3 is a linear or branched alkyl, cycloalkyl or aryl;

R4 is hydrogen, aryl, a linear C1-C15 alkyl or a branched C3-C15 alkyl.

3. A polyisocyanate composition according to claim 2, characterized in that, the isocyanate monomer is selected from aliphatic diisocyanate.

4. A polyisocyanate composition according to claim 2, characterized in that, the catalyst is added in the form of an alcohol solution during the preparation process;

the amount of the catalyst used is 0.001-5% of the mass of the isocyanate monomer.

5. A polyisocyanate composition according to claim 2, characterized in that, the oligomerization is reacted at a temperature of 0° C.-100° C..

6. A polyisocyanate composition according to claim 2, characterized in that, the oligomerization is terminated after converting 5-80 wt% of the isocyanate monomer.

7. A polyisocyanate composition according to claim 1, characterized in that, the polyisocyanate composition is prepared by the oligomerization of at least one kind of isocyanate monomer having a NCO functionality>1 in the presence of a quaternary ammonium salt catalyst which is prepared by a preparation method comprising the following steps:

(1) adding trimethylchlorosilane gradually into a di-substituted secondary amine under ice-water bath condition, after the addition, returning to room temperature and continuing the reaction, after the reaction, adding ice water into the reaction solution to quench the reaction, and separating to obtain an intermediate product a;

(2) adding trimethylchlorosilane gradually into a carboxylic acid under ice-water bath condition, after the addition, returning to room temperature and continuing the reaction, after the reaction, adding ice water into the reaction solution to quench the reaction, and separating to obtain an intermediate product b;

(3) dissolving the separated intermediate product a, intermediate product b and a dimethyl acetal in an alcohol solvent, and reacting at 50-80° C., after the reaction, optionally removing part of the alcohol solvent, and obtaining an alcohol solution containing the quaternary ammonium salt catalyst at a target concentration.

8. A polyisocyanate composition according to claim 1, characterized in that, the molar ratio of allophanate group/(isocyanurate group+allophanate group) is 0.2-0.6; the molar ratio of allophanate group/(allophanate group+urethane group) is 0.2-0.5; the molar ratio of iminooxadiazinedione group/isocyanurate group is 0.01-0.1.

9. A polyisocyanate composition according to claim 3, characterized in that, the isocyanate monomer is selected from is one or more of hexamethylene diisocyanate, 2-methylpentane-1,5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate, isophorone diisocyanate, 1,3- and 1,4-bis(isocyanatomethyl) benzene, and 1,3- and 1,4-bis(isocyanatomethyl)cyclohexane.

10. A polyisocyanate composition according to claim 4, characterized in that, the mass concentration of the catalyst in the alcohol is 0.25%-50%;

the amount of the catalyst used is 0.002-2% of the mass of the isocyanate monomer.

11. A polyisocyanate composition according to claim 5, characterized in that, the oligomerization is reacted at a temperature of 20-90° C..

12. A polyisocyanate composition according to claim 6, characterized in that, the oligomerization is terminated after converting 10-70 wt% of the isocyanate monomer;

the oligomerization is terminated by deactivating the catalyst.

* * * * *